US012796941B2

(12) United States Patent
Zhou et al.

(10) Patent No.: US 12,796,941 B2
(45) Date of Patent: Nov. 17, 2026

(54) BLOOD PRESSURE DETECTION METHOD AND APPARATUS, AND ELECTRONIC DEVICE

(71) Applicant: VIVO MOBILE COMMUNICATION CO., LTD., Guangdong (CN)

(72) Inventors: Xudong Zhou, Guangdong (CN); Zhenyu Long, Guangdong (CN)

(73) Assignee: VIVO MOBILE COMMUNICATION CO., LTD., Guangdong (CN)

( * ) Notice: Subject to any disclaimer, the term of this patent is extended or adjusted under 35 U.S.C. 154(b) by 203 days.

(21) Appl. No.: 18/784,037

(22) Filed: Jul. 25, 2024

(65) Prior Publication Data

US 2024/0374151 A1 Nov. 14, 2024

Related U.S. Application Data

(63) Continuation of application No. PCT/CN2023/072879, filed on Jan. 18, 2023.

(30) Foreign Application Priority Data

Jan. 25, 2022 (CN) ......................... 202210088537.2

(51) Int. Cl.

| | |
|---|---|
| ***A61B 5/021*** | (2006.01) |
| ***A61B 5/00*** | (2006.01) |
| ***A61B 90/00*** | (2016.01) |

(52) U.S. Cl.

CPC ........ *A61B 5/02108* (2013.01); *A61B 5/6898* (2013.01); *A61B 5/743* (2013.01);

(Continued)

(58) Field of Classification Search

CPC ............ A61B 5/02108; A61B 5/02116; A61B 2090/061; A61B 2090/064;

(Continued)

(56) References Cited

U.S. PATENT DOCUMENTS 11,520,375 B2 * 12/2022 Kang ................. A61B 5/02028
2014/0106816 A1 * 4/2014 Shimuta ................. A61B 5/024 455/556.1

(Continued)

FOREIGN PATENT DOCUMENTS

CN 112426140 A * 3/2021 ............. A61B 5/021
CN 113425269 A 9/2021

(Continued)

OTHER PUBLICATIONS

Second European Office Action for European Patent Application No. 23 746 185.0 dated Oct. 17, 2025, 4 pages.

*Primary Examiner* — Eric J Messersmith
(74) *Attorney, Agent, or Firm* — Price Heneveld LLP

(57) ABSTRACT

A blood pressure detection method and apparatus, and an electronic device. The method is applied to an electronic device which is a rollable-display electronic device including a housing assembly, a rollable-display, and a photoplethysmograph (PPG) sensor, and the PPG sensor is arranged on a frame of the housing assembly distributed along an unfolding direction of the rollable-display. The method includes: in a case that a target user holds an area in which the PPG sensor is located, outputting a target torsion force through a reel motor of the electronic device, where the target torsion force is used to drive the rollable-display to unfold (101); in a case that an unfolding length of the rollable-display is maintained in a target length range, obtaining a pulse wave signal detected by the PPG sensor (102); and generating a blood pressure detection result of the target user based on the pulse wave signal (103).

9 Claims, 4 Drawing Sheets

(52) U.S. Cl.
CPC ........ *A61B 90/06* (2016.02); *A61B 2090/061* (2016.02); *A61B 2090/064* (2016.02); *A61B 2560/0406* (2013.01); *A61B 2560/0462* (2013.01); *A61B 2562/0204* (2013.01)

(58) Field of Classification Search
CPC .... A61B 2560/0406; A61B 2560/0462; A61B 2562/0204; A61B 5/6824; A61B 5/6843; A61B 5/6898; A61B 5/743; A61B 5/7445; A61B 90/06; G06F 1/1626; G09G 2380/00; H04M 1/0202
See application file for complete search history.

(56) References Cited

U.S. PATENT DOCUMENTS

| | | | | |
|---|---|---|---|---|
| 2015/0229750 | A1 | 8/2015 | Zhou et al. | |
| 2017/0168769 | A1* | 6/2017 | Jeon | G06F 1/1652 |
| 2020/0085315 | A1* | 3/2020 | Kang | A61B 5/02007 |
| 2021/0022622 | A1* | 1/2021 | Lee | A61B 5/02108 |
| 2021/0365664 | A1* | 11/2021 | Lee | A61B 5/02007 |
| 2021/0386375 | A1* | 12/2021 | Kang | A61B 5/02116 |
| 2024/0366098 | A1* | 11/2024 | Fong | A61B 5/02116 |

FOREIGN PATENT DOCUMENTS

| | | | |
|---|---|---|---|
| CN | 114403828 | A | 4/2022 |
| EP | 3913461 | A1 | 11/2021 |
| JP | 2009201895 | A | 9/2009 |
| WO | 2021098704 | A1 | 5/2021 |

* cited by examiner

BLOOD PRESSURE DETECTION METHOD AND APPARATUS, AND ELECTRONIC DEVICE

CROSS-REFERENCE TO RELATED APPLICATIONS

This application is a Bypass Continuation Application of PCT International Application No. PCT/CN2023/072879 filed on Jan. 18, 2023, which claims priority to Chinese Patent Application No. 202210088537.2, filed on Jan. 25, 2022 in China, which are incorporated herein by reference in their entireties.

TECHNICAL FIELD

This application pertains to the field of blood pressure detection technologies, and in particular, to a blood pressure detection method and apparatus, and an electronic device.

BACKGROUND

With the development of technology, more and more manufacturers select to integrate photoplethysmograph (photoplethysmograph, PPG) sensors on electronic devices such as smart phones, so that users can detect blood pressure changes through electronic devices.

However, compared with the pressure sensor on the conventional cuff blood pressure detector, the blood pressure detection scheme of the PPG sensor using the electronic device lacks an air pump to provide appropriate pressure, which makes it difficult for users to control the pressing pressure within the pressure range required for blood pressure detection, and further leads to the decline of detection accuracy.

It can be seen that the blood pressure detection scheme in the related art has the problem of low detection accuracy.

SUMMARY

According to a first aspect, an embodiment of this application provides a blood pressure detection method, applied to an electronic device, where the electronic device is a rollable-display electronic device including a housing assembly, a rollable-display, and a photoplethysmograph (PPG) sensor, the PPG sensor is arranged on a frame of the housing assembly distributed along an unfolding direction of the rollable-display, and the method includes:

- in a case that a target user holds an area in which the PPG sensor is located, outputting a target torsion force through a reel motor of the electronic device, where the target torsion force is used to drive the rollable-display to unfold;
- in a case that an unfolding length of the rollable-display is maintained in a target length range, obtaining a pulse wave signal detected by the PPG sensor; and
- generating a blood pressure detection result of the target user based on the pulse wave signal.

According to a second aspect, an embodiment of this application provides a blood pressure detection apparatus, applied to an electronic device, where the electronic device is a rollable-display electronic device including a housing assembly, a rollable-display, and a PPG sensor, the PPG sensor is arranged on a frame of the housing assembly distributed along an unfolding direction of the rollable-display, and the apparatus includes:

- a first output module, configured to: in a case that a target user holds an area in which the PPG sensor is located, output a target torsion force through a reel motor of the electronic device, where the target torsion force is used to drive the rollable-display to unfold;
- an obtaining module, configured to: in a case that an unfolding length of the rollable-display is maintained in a target length range, obtain a pulse wave signal detected by the PPG sensor; and
- a generating module, configured to generate a blood pressure detection result of the target user based on the pulse wave signal.

According to a third aspect, an embodiment of this application provides an electronic device, where the electronic device includes a processor and a memory, the memory stores a program or an instruction that can run on the processor, and when the program or the instruction is executed by the processor, the steps of the method according to the first aspect are implemented.

According to a fourth aspect, an embodiment of this application provides a readable storage medium. The readable storage medium stores a program or an instruction, where when the program or the instruction is executed by a processor, the steps of the method according to the first aspect are implemented.

According to a fifth aspect, an embodiment of this application provides a chip. The chip includes a processor and a communications interface, the communications interface is coupled to the processor, and the processor is configured to run a program or an instruction to implement the method according to the first aspect.

According to a sixth aspect, an embodiment of this application provides a computer program product. The program product is stored in a storage medium, and the program product is executed by at least one processor to implement the method according to the first aspect.

DESCRIPTION OF EMBODIMENTS

Figure 1:
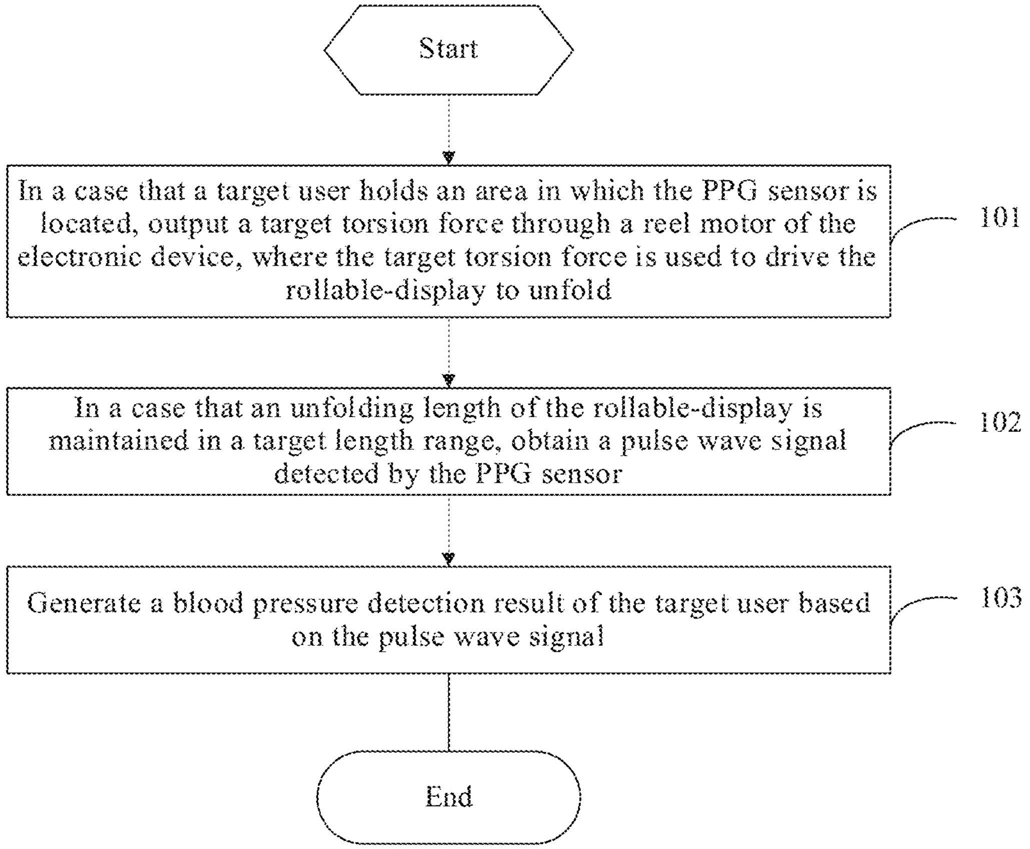
FIG. 1 is a flowchart of a blood pressure detection method according to an embodiment of this application.

The following clearly and completely describes the technical solutions in the embodiments of this application with reference to the accompanying drawings in the embodiments of this application. Apparently, the described embodiments are some but not all of the embodiments of this application. All other embodiments obtained by a person of ordinary skill in the art based on the embodiments of this application without creative efforts shall fall within the protection scope of this application.

In the specification and claims of this application, the terms such as “first” and “second” are used for distinguishing similar objects, and are not necessarily used to describe a particular order or sequence. It should be understood that terms used in such a way are interchangeable in proper circumstances, so that embodiments of this application can be implemented in an order other than the order illustrated or described herein. Objects classified by “first”, “second”, and the like are usually of a same type, and a quantity of objects is not limited. For example, there may be one or more first objects. In addition, in this specification and the claims, “and/or” indicates at least one of connected objects, and a character “/” generally indicates an “or” relationship between associated objects.

With reference to the accompanying drawings, the blood pressure detection method provided in the embodiments of this application is described in detail by using specific embodiments and application scenarios thereof.

The blood pressure detection method provided in the embodiments of this application is applied to an electronic device, where the electronic device is a rollable-display electronic device including a housing assembly, a rollable-display, and a PPG sensor, the PPG sensor is arranged on a frame of the housing assembly distributed along an unfolding direction of the rollable-display.

Optionally, the housing assembly includes a first housing and a second housing, the first housing and the second housing are connected in a sliding way, one end of the rollable-display is connected to the first housing, and the other end of the rollable-display is connected to the second housing. Driven by a reel motor, the rollable-display is retractable and can be switched between an unfolded state and a folded state.

In the unfolding process of the rollable-display, the first housing and/or the second housing can be driven by the reel motor to move, and then the rollable-display is driven to unfold. It is also possible to drive the rollable-display to unfold through the reel motor, and then drive the first housing and the second housing to move in opposite directions, so as to realize the unfolding process of the rollable-display.

The PPG sensor is used for the pulse wave signal in the arterial capillary of the user, and the detected pulse wave signal can be calculated to obtain corresponding systolic and diastolic blood pressure results based on a corresponding algorithm, that is, corresponding blood pressure detection results can be calculated.

In this application, in the process of blood pressure detection, the user can hold a position where the PPG sensor is arranged in the housing assembly. Moreover, in order to facilitate the user to quickly locate the PPG sensor on the housing assembly, a reminder sign, such as “PPG”, can also be displayed at the position where the PPG sensor is arranged on the housing assembly to remind the user.

Referring to FIG. 1, FIG. 1 is a flowchart of a blood pressure detection method according to an embodiment of this application. As shown in FIG. 1, the method includes the following steps.

Step 101. In a case that a target user holds an area in which the PPG sensor is located, output a target torsion force through a reel motor of the electronic device, where the target torsion force is used to drive the rollable-display to unfold.

In this step, the target torsion force can be understood as a driving force that can drive the rollable-display to unfold, that is, the target torsion force is greater than a static friction force of the rollable-display and can drive the rollable-display to enter the unfolded state.

Step 102. In a case that an unfolding length of the rollable-display is maintained in a target length range, obtain a pulse wave signal detected by the PPG sensor.

In this step, in a case that the unfolding length of the rollable-display is maintained in the target length range, it can be understood that the target torsion force output by the reel motor is balanced with the holding force of the target user, so that the unfolding length of the rollable-display is maintained in a length range. That is, the relationship between the target torsion force and the holding force of the target user can be determined by detecting whether the unfolding length of the rollable-display is maintained in the target length range, and then the holding force of the user can be determined.

Because in the process of blood pressure detection, the target user needs to maintain the pressing force within the pressure range required for blood pressure detection, to improve the accuracy of blood pressure detection, the pressing force of the target user can be adjusted by controlling the target torsion force, so that the target user can maintain the pressing force within the pressure range required for blood pressure detection, and then the purpose of improving the accuracy of blood pressure detection can be achieved.

It can be understood that the target torsion force in this application is used to maintain the pressing force of the target user within the pressure range required for blood pressure detection.

Specifically, it can be determined whether the target torsion force output by the reel motor is in balance with the holding force of the target user (that is, the pressing force of the target user on the PPG sensor) by determining whether the unfolding length of the rollable-display is maintained in the target length range. When it is determined that the unfolding length of the rollable-display is maintained in the target length range, it is determined that the target torsion force output by the reel motor is in balance with the holding force of the target user, that is, the pressing force of the target user on the PPG sensor is within the pressure range required for blood pressure detection, thereby achieving the purpose of improving the accuracy of blood pressure detection.

Step 103. Generate a blood pressure detection result of the target user based on the pulse wave signal.

In this step, the blood pressure detection result includes a systolic blood pressure result and a diastolic blood pressure result, and the systolic blood pressure result and the diastolic blood pressure result can be calculated by fitting a virtual envelope curve based on the pulse wave signal.

In this way, by using the characteristics of the rollable-display electronic device, the holding power of the user can be maintained, based on the unfolding tension of the rollable-display of the rollable-display electronic device, within the pressure range required for blood pressure detection, so as to achieve the purpose of improving the accuracy of blood pressure detection.

Moreover, compared with the electronic device in the related art, a pressure detection sensor is added to detect the pressing force of the user, and a component layout of the electronic device can be simplified.

Because the pressure required for blood pressure detection is a range, the target torsion force of different ranges can be set, and detection results corresponding to different ranges can be obtained. Then the virtual envelope curve is fitted based on the detection results of different ranges, and the systolic blood pressure result and the diastolic blood pressure result are finally obtained through the envelope curve, so as to improve the accuracy of blood pressure detection.

In the process of blood pressure detection, the PPG sensor can collect pulse wave signals in the whole process, but in the process of generating detection results, only pulse wave signals that meet the condition are extracted to achieve the purpose of improving the accuracy of blood pressure detection.

Figure 2:
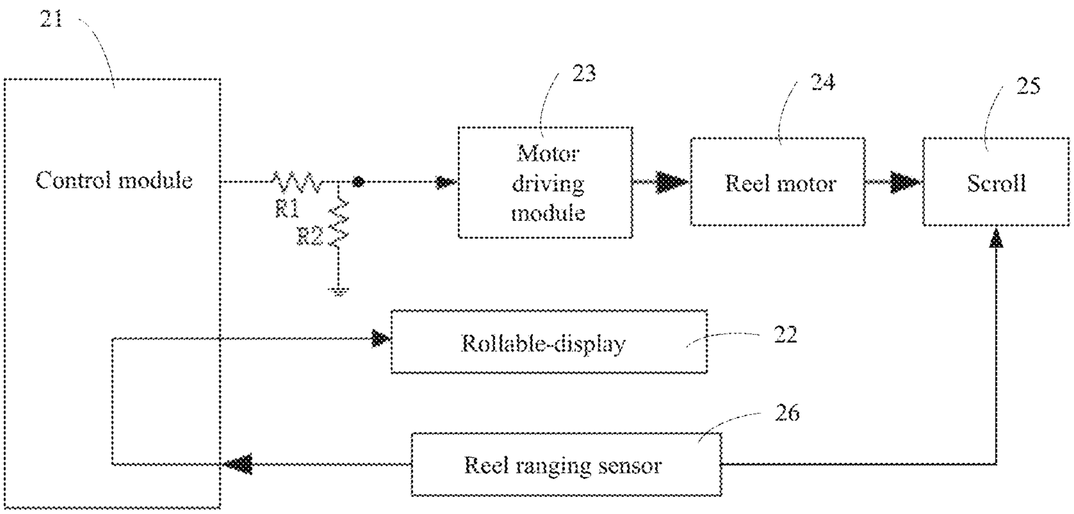
FIG. 2 is a structural diagram of an electronic device according to an embodiment of this application.

As shown in FIG. 2, an embodiment of this application further provides a block diagram of an electronic device. The electronic device includes a control module 21, a rollable-display 22, a motor driving module 23, a reel motor 24, a reel 25, and a reel ranging sensor 26.

The control module 21 is separately electrically connected to the rollable-display 22, the motor driving module 23, and the reel ranging sensor 26. The motor driving module 23 is electrically connected to the reel motor 24.

The reel motor 24 is drivingly connected to the reel 25, and the reel ranging sensor 26 is arranged on the reel 25.

The reel ranging sensor 26 is used to detect the unfolding length of the rollable-display 22. Specifically, the unfolding length of the rollable-display 22 can be calculated by detecting a distance between the PPG sensor and the reel 25.

The reel motor 24 is used to drive the reel 25 to be unfolded or folded, so that the rollable-display can be switched between the unfolded state and the folded state.

In some implementations, the reel ranging sensor 26 can form a closed-loop control with the rollable-display 22 through the control module 21, so as to display the detection result of the reel ranging sensor 26 in real time through the rollable-display 22.

Optionally, in a case that an unfolding length of the rollable-display is maintained in a target length range, the obtaining a pulse wave signal detected by the PPG sensor includes:

in a case that the unfolding length of the rollable-display is maintained in the target length range, and the unfolding length of the rollable-display is maintained in the target length range for duration exceeding a first preset time, obtaining a pulse wave signal detected by the PPG sensor in a time period corresponding to the first preset time.

In this implementation, it is determined whether the target torsion force output by the reel motor is in balance with the holding force of the target user by determining the duration that the unfolding length of the rollable-display is maintained in the target length range, and it is determined that the target torsion force output by the reel motor is in balance with the holding force of the target user when the unfolding length of the rollable-display is maintained in the target length range for duration exceeding a first preset time (for example, 10 seconds), so as to improve the accuracy of the pulse wave signal detected by the PPG sensor and further achieve the purpose of improving the accuracy of blood pressure detection.

Optionally, after the outputting a target torsion force through a reel motor of the electronic device, in a case that an unfolding length of the rollable-display is maintained in a target length range, before the obtaining a pulse wave signal detected by the PPG sensor, the method further includes:

- detecting a change of the unfolding length of the rollable-display; and
- in a case that the change of the unfolding length meets a preset condition, outputting prompt information, where the prompt information is used to remind the target user to adjust a holding force and maintain the unfolding length of the rollable-display in the target length range.

In this implementation, it can be determined whether the unfolding length of the rollable-display is maintained in the target length range by detecting the change of the unfolding length of the rollable-display, and then whether the target torsion force output by the reel motor is in balance with the holding force of the target user is determined.

In some implementations, the change of the unfolding length of the rollable-display can be detected by using the reel ranging sensor shown in FIG. 2.

When the change of the unfolding length of the rollable-display meets the preset condition, it can be understood that the unfolding length of the rollable-display is not maintained within the target length range, that is, the holding force of the target user is too large or too small relative to the target torsion force.

Specifically, when the change of the unfolding length of the rollable-display indicates that the unfolding length of the rollable-display is greater than a maximum length of the target length range, prompt information is used to instruct the target user to increase the holding power and maintain the unfolding length of the rollable-display in the target length range, that is, maintain the rollable-display from unfolding and folding. Accordingly, when the change of the unfolding length of the rollable-display indicates that the unfolding length of the rollable-display is less than a minimum length of the target length range, the prompt information is used to instruct the target user to reduce the holding power and maintain the unfolding length of the rollable-display in the target length range, that is, maintain the rollable-display from unfolding and folding.

In addition, when the change of the unfolding length of the rollable-display indicates that the unfolding length of the rollable-display is maintained within the target length range, the prompt information is used to instruct the target user to maintain the holding power and maintain the rollable-display from unfolding and folding.

The prompt information can be output by voice playing to instruct the user to perform corresponding operations.

Optionally, the method further includes:

- displaying blood pressure detection information on the rollable-display, where the blood pressure detection information includes at least one of the following:
- a curve diagram of the target torsion force and the holding force of the target user;
- a countdown diagram of maintaining the holding force by the target user;
- a holding operation diagram; and
- the prompt information.

In this implementation, by displaying the blood pressure detection information in real time, especially the information such as the curve diagram of the target torsion force and the holding force of the target user, the countdown diagram of maintaining the holding force by the target user, the holding operation diagram, and the prompt information, it is convenient for the target user to adjust the blood pressure detection operation in time and improve the blood pressure detection experience of the user.

In some embodiments, the detection duration can be set to 10 seconds, that is, the duration for the user to maintain the holding power can be set to 10 seconds, and the countdown diagram of maintaining the holding force by the target user can be displayed on the rollable-display, so that the user can maintain the holding power, thereby achieving the purpose of improving the accuracy of the detection result.

Figure 3A:
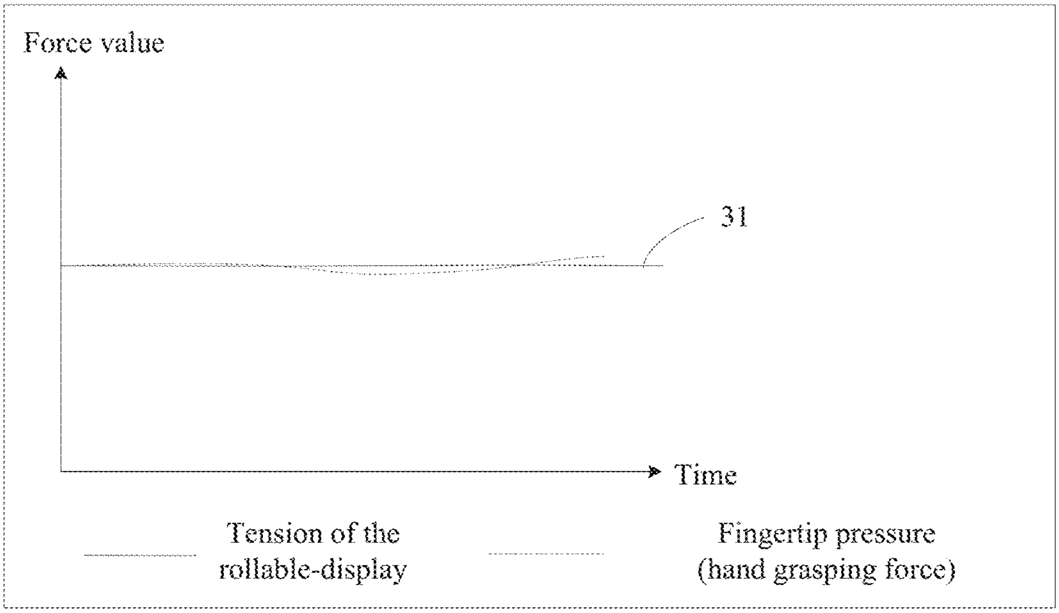
FIG. 3*a* is a first schematic diagram of blood pressure detection operations according to an embodiment of this application.
Figure 3B:
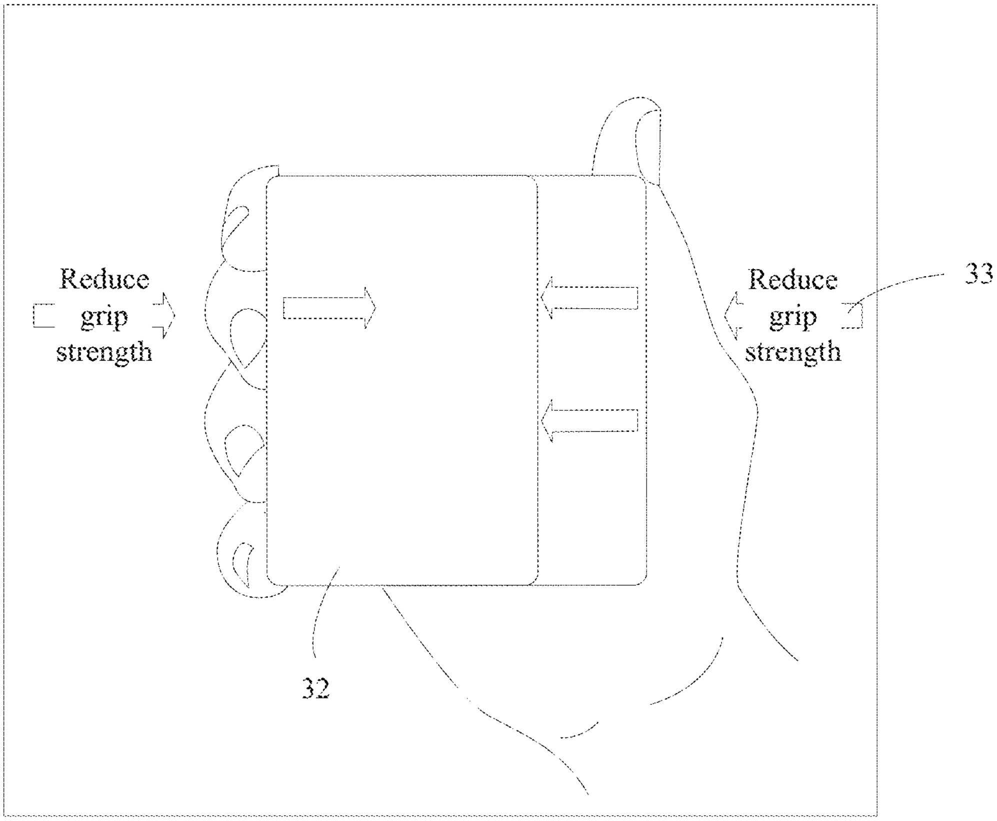
FIG. 3*b* is a second schematic diagram of blood pressure detection operations according to an embodiment of this application.

As shown in FIG. 3*a*, a curve diagram 31 of the target torsion force and the holding force of the target user can be displayed on the display interface of the rollable-display. As shown in FIG. 3*b*, a holding operation diagram 32 and the prompt information 33 can also be displayed on the display interface of the rollable-display.

According to the blood pressure detection method provided in the embodiments of this application, in a case that a target user holds an area in which the PPG sensor is located, a target torsion force is output through a reel motor of the electronic device, where the target torsion force is used to drive the rollable-display to unfold; in a case that an unfolding length of the rollable-display is maintained in a target length range, a pulse wave signal detected by the PPG sensor is obtained; and a blood pressure detection result of the target user is generated based on the pulse wave signal. In this way, by using the characteristics of the rollable-display electronic device, the holding power of the user can be maintained, based on the unfolding tension of the rollable-display of the rollable-display electronic device, within the pressure range required for blood pressure detection, so as to achieve the purpose of improving the accuracy of blood pressure detection.

The blood pressure detection method provided in this embodiment of this application may be executed by a blood pressure detection apparatus. In this embodiment of this application, the blood pressure detection apparatus provided in the embodiments of this application is described by using an example in which the blood pressure detection method is performed by the blood pressure detection apparatus.

Figure 4:
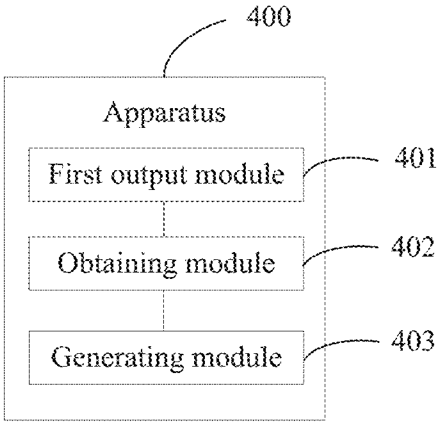
FIG. 4 is a structural diagram of a blood pressure detection apparatus according to an embodiment of this application.

Referring to FIG. 4, FIG. 4 is a structural diagram of a blood pressure detection apparatus according to an embodiment of this application. As shown in FIG. 4, the apparatus 400 is applied to an electronic device, the electronic device is a rollable-display electronic device including a housing assembly, a rollable-display, and a PPG sensor, the PPG sensor is arranged on a frame of the housing assembly distributed along an unfolding direction of the rollable-display, and the apparatus 400 includes:

a first output module 401, configured to: in a case that a target user holds an area in which the PPG sensor is located, output a target torsion force through a reel motor of the electronic device, where the target torsion force is used to drive the rollable-display to unfold;

an obtaining module 402, configured to: in a case that an unfolding length of the rollable-display is maintained in a target length range, obtain a pulse wave signal detected by the PPG sensor; and a generating module 403, configured to generate a blood pressure detection result of the target user based on the pulse wave signal.

Optionally, the obtaining module 402 is specifically configured to: in a case that the unfolding length of the rollable-display is maintained in the target length range, and the unfolding length of the rollable-display is maintained in the target length range for duration exceeding a first preset time, obtain a pulse wave signal detected by the PPG sensor in a time period corresponding to the first preset time.

Optionally, the apparatus 400 further includes:

a detecting module, configured to detect a change of the unfolding length of the rollable-display; and a second output module, configured to: in a case that the change of the unfolding length meets a preset condition, output prompt information, where the prompt information is used to remind the target user to adjust a holding force and maintain the unfolding length of the rollable-display in the target length range.

Optionally, the apparatus 400 further includes:

a display module, configured to display blood pressure detection information on the rollable-display, where the blood pressure detection information includes at least one of the following:

a curve diagram of the target torsion force and the holding force of the target user;

a countdown diagram of maintaining the holding force by the target user;

a holding operation diagram; and the prompt information.

Optionally, the second output module is specifically configured to output prompt information by voice playing.

The blood pressure detection apparatus in this embodiment of this application may be an electronic device, or may be a component such as a circuit or a chip in the electronic device. The electronic device may be a terminal, or another device other than the terminal. For example, the electronic device may be a mobile phone, a tablet computer, a notebook computer, a palmtop computer, an in-vehicle electronic device, a mobile Internet device (Mobile Internet Device, MID), an augmented reality (Augmented Reality, AR)/virtual reality (Virtual Reality, VR) device, a robot, a wearable device, an ultra-mobile personal computer (Ultra-Mobile Personal Computer, UMPC), a netbook, a personal digital assistant (Personal Digital Assistant, PDA), or the like. The electronic device may be alternatively a network attached storage (Network Attached Storage, NAS), a personal computer (Personal Computer, PC), a television (Television, TV), a teller machine, a self-service machine, or the like. This is not specifically limited in this embodiment of this application.

The blood pressure detection apparatus in this embodiment of this application may be an apparatus with an operating system. The operating system may be an Android (Android) operating system, may be an iOS operating system, or may be another possible operating system. This is not specifically limited in this embodiment of this application.

The blood pressure detection apparatus provided in this embodiment of this application can implement processes implemented in the method embodiments from FIG. 1 to FIG. 3. To avoid repetition, details are not described herein again.

Figure 5:
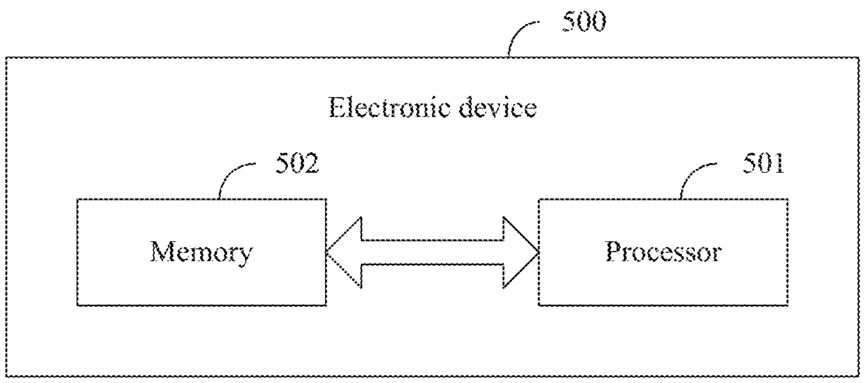
FIG. 5 is a structural diagram of an electronic device according to another embodiment of this application.

Optionally, as shown in FIG. 5, an embodiment of this application further provides an electronic device 500, including a processor 501 and a memory 502, and the memory 502 stores a program or an instruction that can be run on the processor 501. When the program or the instruction is executed by the processor 501, the steps of the foregoing embodiment of the blood pressure detection method are implemented, and a same technical effect can be achieved. To avoid repetition, details are not described herein again.

It should be noted that the electronic device in this embodiment of this application includes the foregoing mobile electronic device and the foregoing non-mobile electronic device.

Figure 6:
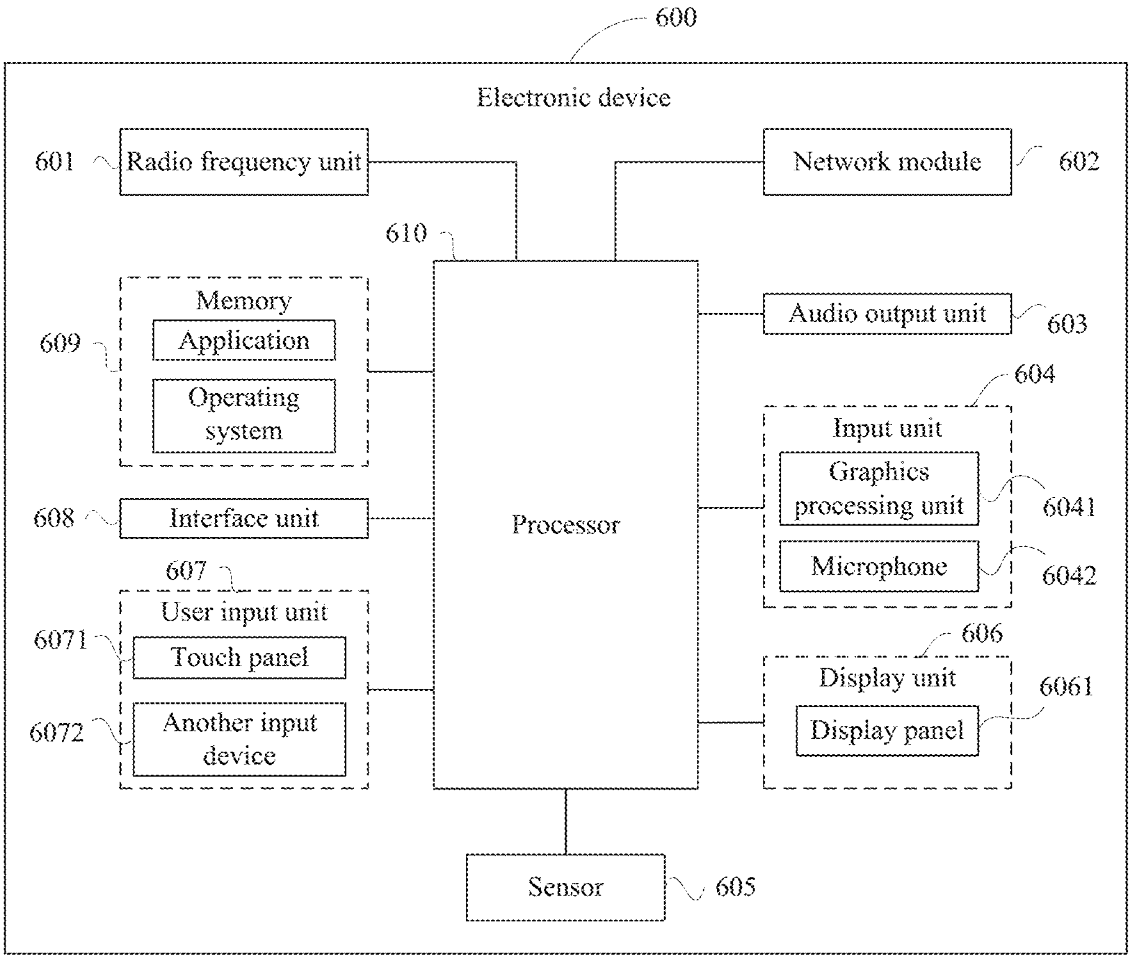
FIG. 6 is a structural diagram of an electronic device according to still another embodiment of this application.

Referring to FIG. 6, FIG. 6 is a structural diagram of an electronic device according to an embodiment of this application. As shown in FIG. 6, the electronic device 600 includes, but not limited to: a radio frequency unit 601, a network module 602, an audio output unit 603, an input unit 604, a sensor 605, a display unit 606, a user input unit 607, an interface unit 608, a memory 609, a processor 610, and the like.

A person skilled in the art can understand that the electronic device 600 may further include a power supply (such as a battery) that supplies power to each component. The power supply may be logically connected to the processor 610 by using a power supply management system, to implement functions such as charging and discharging management, and power consumption management by using the power supply management system. The structure of the electronic device shown in FIG. 6 does not constitute a limitation on the electronic device. The electronic device may include components more or fewer than those shown in the diagram, a combination of some components, or different component arrangements. Details are not described herein.

The processor 610 is configured to: in a case that a target user holds an area in which the PPG sensor is located, output a target torsion force through a reel motor of the electronic device, where the target torsion force is used to drive the rollable-display to unfold; in a case that an unfolding length of the rollable-display is maintained in a target length range, obtain a pulse wave signal detected by the PPG sensor; and generate a blood pressure detection result of the target user based on the pulse wave signal.

Optionally, the processor 610 is configured to: in a case that the unfolding length of the rollable-display is maintained in the target length range, and the unfolding length of the rollable-display is maintained in the target length range for duration exceeding a first preset time, obtain a pulse wave signal detected by the PPG sensor in a time period corresponding to the first preset time.

Optionally, the sensor 605 is configured to detect a change of the unfolding length of the rollable-display; and the processor 610 is configured to: in a case that the change of the unfolding length meets a preset condition, output prompt information, where the prompt information is used to remind the target user to adjust a holding force and maintain the unfolding length of the rollable-display in the target length range.

Optionally, the display unit 606 is configured to display blood pressure detection information on the rollable-display, where the blood pressure detection information includes at least one of the following:

a curve diagram of the target torsion force and the holding force of the target user;

a countdown diagram of maintaining the holding force by the target user;

a holding operation diagram; and the prompt information.

Optionally, the audio output unit 603 is configured to output prompt information by voice playing.

It should be understood that in this embodiment of this application, the input unit 604 may include a graphics processing unit (Graphics Processing Unit, GPU) 6041 and a microphone 6042. The graphics processing unit 6041 processes image data of a static picture or a video obtained by an image capture apparatus (for example, a camera) in a video capture mode or an image capture mode. The display unit 606 may include a display panel 6061, and the display panel 6061 may be configured in a form of a liquid crystal display, an organic light-emitting diode, or the like. The user input unit 607 includes at least one of a touch panel 6071 and another input device 6072. The touch panel 6071 is also referred to as a touchscreen. The touch panel 6071 may include two parts: a touch detection apparatus and a touch controller. The another input device 6072 may include but is not limited to a physical keyboard, a functional button (such as a volume control button or a power on/off button), a trackball, a mouse, and a joystick. Details are not described herein.

The memory 609 may be configured to store a software program and various data. The memory 609 may mainly include a first storage area for storing a program or an instruction and a second storage area for storing data. The first storage area may store an operating system, and an application or an instruction required by at least one function (for example, a sound playing function or an image playing function). In addition, the memory 609 may be a volatile memory or a non-volatile memory, or the memory 609 may include a volatile memory and a non-volatile memory. The non-volatile memory may be a read-only memory (Read-Only Memory, ROM), a programmable read-only memory (Programmable ROM, PROM), an erasable programmable read-only memory (Erasable PROM, EPROM), an electrically erasable programmable read-only memory (Electrically EPROM, EEPROM), or a flash memory. The volatile memory may be a random access memory (Random Access Memory, RAM), a static random access memory (Static RAM, SRAM), a dynamic random access memory (Dynamic RAM, DRAM), a synchronous dynamic random access memory (Synchronous DRAM, SDRAM), a double data rate synchronous dynamic random access memory (Double Data Rate SDRAM, DDRSDRAM), an enhanced synchronous dynamic random access memory (Enhanced SDRAM, ESDRAM), a synchlink dynamic random access memory (Synchlink DRAM, SLDRAM), and a direct rambus random access memory (Direct Rambus RAM, DRRAM). The memory 609 in this embodiment of this application includes but is not limited to these memories and any memory of another proper type.

The processor 610 may include one or more processing units. Optionally, an application processor and a modem processor are integrated into the processor 610. The application processor mainly processes an operating system, a user interface, an application, or the like. The modem processor mainly processes a wireless communication signal, for example, a baseband processor. It may be understood that, alternatively, the modem processor may not be integrated into the processor 610.

An embodiment of this application further provides a readable storage medium. The readable storage medium stores a program or an instruction. When the program or the instruction is executed by a processor, the processes of the foregoing blood pressure detection method embodiment are implemented, and same technical effect can be achieved. To avoid repetition, details are not described herein again.

The processor is a processor in the electronic device in the foregoing embodiment. The readable storage medium includes a computer-readable storage medium, such as a computer read-only memory ROM, a random access memory RAM, a magnetic disk, or an optical disc.

An embodiment of this application further provides a chip. The chip includes a processor and a communications interface, the communications interface is coupled to the processor, and the processor is configured to run a program or an instruction to implement the processes of the foregoing blood pressure detection method embodiment, and same technical effect can be achieved. To avoid repetition, details are not described herein again.

It should be understood that the chip mentioned in this embodiment of this application may also be referred to as a system-level chip, a system chip, a chip system, an on-chip system chip, or the like.

An embodiment of this application provides a computer program product. The program product is stored in a storage medium. The program product is executed by at least one processor to implement the processes of the foregoing blood pressure detection method embodiment, and same technical effect can be achieved. To avoid repetition, details are not described herein again.

It should be noted that, in this specification, the term “include”, “comprise”, or any other variant thereof is intended to cover a non-exclusive inclusion, so that a process, a method, an article, or an apparatus that includes a list of elements not only includes those elements but also includes other elements which are not expressly listed, or further includes elements inherent to this process, method, article, or apparatus. In absence of more constraints, an element preceded by “includes a . . . ” does not preclude the existence of other identical elements in the process, method, article, or apparatus that includes the element. In addition, it should be noted that the scope of the method and the apparatus in the implementations of this application is not limited to performing functions in an illustrated or discussed sequence, and may further include performing functions in a basically simultaneous manner or in a reverse sequence according to the functions concerned. For example, the described method may be performed in an order different from that described, and the steps may be added, omitted, or combined. In addition, features described with reference to some examples may be combined in other examples.

Based on the descriptions of the foregoing implementations, a person skilled in the art may clearly understand that the method in the foregoing embodiment may be implemented by software in addition to a necessary universal hardware platform or by hardware only. In most circumstances, the former is a preferred implementation. Based on such an understanding, the technical solutions of this application essentially or the part contributing to the prior art may be implemented in a form of a computer software product. The computer software product is stored in a storage medium (for example, a ROM/RAM, a floppy disk, or an optical disc), and includes several instructions for instructing a terminal (which may be a mobile phone, a computer, a server, a network device, or the like) to perform the methods described in the embodiments of this application.

The embodiments of this application are described above with reference to the accompanying drawings, but this application is not limited to the foregoing specific implementations, and the foregoing specific implementations are only illustrative and not restrictive. Under the enlightenment of this application, a person of ordinary skill in the art can make many forms without departing from the purpose of this application and the protection scope of the claims, all of which fall within the protection of this application.

The invention claimed is:

1. A blood pressure detection method, applied to an electronic device, wherein the electronic device is a rollable-display electronic device comprising a housing assembly, a rollable-display, and a photoplethysmograph (PPG) sensor, the PPG sensor is arranged on a frame of the housing assembly distributed along an unfolding direction of the rollable-display, and the method comprises:

in a case that a target user holds an area in which the PPG sensor is located, outputting a target torsion force through a reel motor of the electronic device, wherein the target torsion force is used to drive the rollable-display to unfold;

in a case that an unfolding length of the rollable-display is maintained in a target length range, obtaining a pulse wave signal detected by the PPG sensor; and generating a blood pressure detection result of the target user based on the pulse wave signal.

2. The method according to claim 1, wherein in a case that an unfolding length of the rollable-display is maintained in a target length range, the obtaining a pulse wave signal detected by the PPG sensor comprises:

in a case that the unfolding length of the rollable-display is maintained in the target length range, and the unfolding length of the rollable-display is maintained in the target length range for duration exceeding a first preset time, obtaining a pulse wave signal detected by the PPG sensor in a time period corresponding to the first preset time.

3. The method according to claim 1, wherein after the outputting a target torsion force through a reel motor of the electronic device, in a case that an unfolding length of the rollable-display is maintained in a target length range, before the obtaining a pulse wave signal detected by the PPG sensor, the method further comprises:

detecting a change of the unfolding length of the rollable-display; and in a case that the change of the unfolding length meets a preset condition, outputting prompt information, wherein the prompt information is used to remind the target user to adjust a holding force and maintain the unfolding length of the rollable-display in the target length range.

4. The method according to claim 3, wherein the method further comprises:

displaying blood pressure detection information on the rollable-display, wherein the blood pressure detection information comprises at least one of the following:

a curve diagram of the target torsion force and the holding force of the target user;

a countdown diagram of maintaining the holding force by the target user;

a holding operation diagram; and the prompt information.

5. An electronic device, comprising a processor, a memory, a rollable-display, a reel motor and a photoplethysmograph (PPG) sensor, wherein the memory stores a program or an instruction that can be run on the processor, and the program or the instruction is executed by the processor to implement:

in a case that a target user holds an area in which the PPG sensor is located, outputting a target torsion force through the reel motor, wherein the target torsion force is used to drive the rollable-display to unfold;

in a case that an unfolding length of the rollable-display is maintained in a target length range, obtaining a pulse wave signal detected by the PPG sensor; and generating a blood pressure detection result of the target user based on the pulse wave signal.

6. The electronic device according to claim 5, wherein in a case that an unfolding length of the rollable-display is maintained in a target length range, when obtaining a pulse wave signal detected by the PPG sensor, the program or the instruction is executed by the processor to implement:

in a case that the unfolding length of the rollable-display is maintained in the target length range, and the unfolding length of the rollable-display is maintained in the target length range for duration exceeding a first preset time, obtaining a pulse wave signal detected by the PPG sensor in a time period corresponding to the first preset time.

7. The electronic device according to claim 5, wherein after the outputting a target torsion force through a reel motor of the electronic device, in a case that an unfolding length of the rollable-display is maintained in a target length range, before the obtaining a pulse wave signal detected by the PPG sensor, the program or the instruction is executed by the processor to implement:

detecting a change of the unfolding length of the rollable-display; and in a case that the change of the unfolding length meets a preset condition, outputting prompt information, wherein the prompt information is used to remind the target user to adjust a holding force and maintain the unfolding length of the rollable-display in the target length range.

8. The electronic device according to claim 7, wherein the program or the instruction is executed by the processor to implement:

displaying blood pressure detection information on the rollable-display, wherein the blood pressure detection information comprises at least one of the following:

a curve diagram of the target torsion force and the holding force of the target user;

a countdown diagram of maintaining the holding force by the target user;

a holding operation diagram; and the prompt information.

9. A readable storage medium, wherein the readable storage medium stores a program or an instruction, and when the program or the instruction is executed by a processor, steps of the blood pressure detection method according to claim 1 are implemented.

* * * * *